US00PP36929P2

(12) United States Plant Patent
van Langen

(10) Patent No.: US PP36,929 P2
(45) Date of Patent: Sep. 2, 2025

(54) ***ALOE* PLANT NAMED 'AMIAL2136'**

(50) Latin Name: ***A. vera* x *A. arborescens***
Varietal Denomination: AMIAL2136

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 18/831,328

(22) Filed: Nov. 18, 2024

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
CPC ..... A01H 5/12; A01H 5/00; A01H 6/00
See application file for complete search history.

(56) References Cited

PUBLICATIONS

CPVO Version 4.22.4 retrieved on Jan. 30, 2025 at https://online.plantvarieties.eu/publicConsultationDetails?registerId=20211783&denomination=amial2136, 2 pp. (Year: 2025).*
Floral Daily 2023 Amigo Plant introduces Aloe Medivera, retrieved on Jan. 30, 2025 at https://www.floraldaily.com/article/9569321/amigo-plant-introduces-aloe-medivera/, 5 pp. (Year: 2023).*
RHS 2025 Aloe Equator ('Amial2136'), retrieved on Jan. 30, 2025 at https://www.rhs.org.uk/plants/527146/aloe-equator-(-amial2136-)/details, one page. (Year: 2025).*

* cited by examiner

*Primary Examiner* — June Hwu
(74) *Attorney, Agent, or Firm* — Samuel R. McCoy, Jr.

(57) ABSTRACT

A new and distinct variety of *Aloe* plant named 'AMIAL2136' which is characterized by succulent foliage arranged in a basal rosette and held upright to outward, dark green lanceolate foliage with spine-like teeth evenly spaced along the margins, mature foliage in the lower whorls of the rosette which are sparsely to moderately covered with small orbicular protuberances arranged in irregular longitudinal rows on the abaxial surface, and the stability of these characteristics from generation to generation.

3 Drawing Sheets

Latin name of the genus and species: The Latin name of the genus and species of the novel variety disclosed herein is *A. vera* x *A. arborescens.*

Variety denomination: The inventive variety of *Aloe* disclosed herein has been given the variety denomination 'AMIAL2136'.

BACKGROUND OF THE INVENTION

Parentage: 'AMIAL2136' is a seedling selection resulting from the controlled pollination of an unnamed *Aloe vera* plant (unpatented), the seed parent, and an unnamed *Aloe arborescens* plant (unpatented), the pollen parent. The crossing was made by the inventor in the spring of 2019 at a commercial greenhouse in Heerhugowaard, the Netherlands. In the spring of 2020, one seedling that was observed exhibited an abundance of small light yellow-green orbicular protuberances loosely arranged in irregular longitudinal rows on the abaxial surface the dark green foliage when compared to the parent plants and all other progenies. The mutation was noted for its unique foliage color and growth habit and was subsequently isolated for further evaluation to confirm the distinctness and stability of the characteristics first observed. Upon confirmation of distinctness and stability, 'AMIAL2136' was selected for commercialization.

Asexual Reproduction: Asexual reproduction of the new cultivar 'AMIAL2136', by way of rooting leaf cuttings, was first initiated in the summer of 2020 at the inventor's commercial greenhouse in Heerhugowaard, the Netherlands.

Through five subsequent generations, the unique features of this cultivar have proven to be stable and true to type.

SUMMARY OF THE INVENTION

The cultivar 'AMIAL2136' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIAL2136'. These characteristics in combination distinguish 'AMIAL2136' as a new and distinct *Aloe vera* plant:

1. 'AMIAL2136' exhibits a large rosette of succulent foliage which gives rise to a plurality of secondary rosettes as the plant ages; and
2. 'AMIAL2136' exhibits dark green succulent foliage which is held upright and slightly outward, with the distalmost portions of laminas curled outward; and
3. 'AMIAL2136' exhibits an adaxial foliar surface that is devoid of protuberances; and
4. 'AMIAL2136' exhibits an abaxial foliar surface that is devoid of protuberances with the exception of the oldest foliage in the outer whorls of the rosette which occasionally exhibits a sparce to moderate abundance of small yellow-green protuberances that are loosely arranged in irregular longitudinal rows; and 5. 'AMIAL2136' exhibits dentate leaf margins with an abundance of prominent spine-like teeth that are colored light greyed-green, generally appearing as a near-white color.

BOTANICAL DESCRIPTION OF THE PLANT

Figure 1:
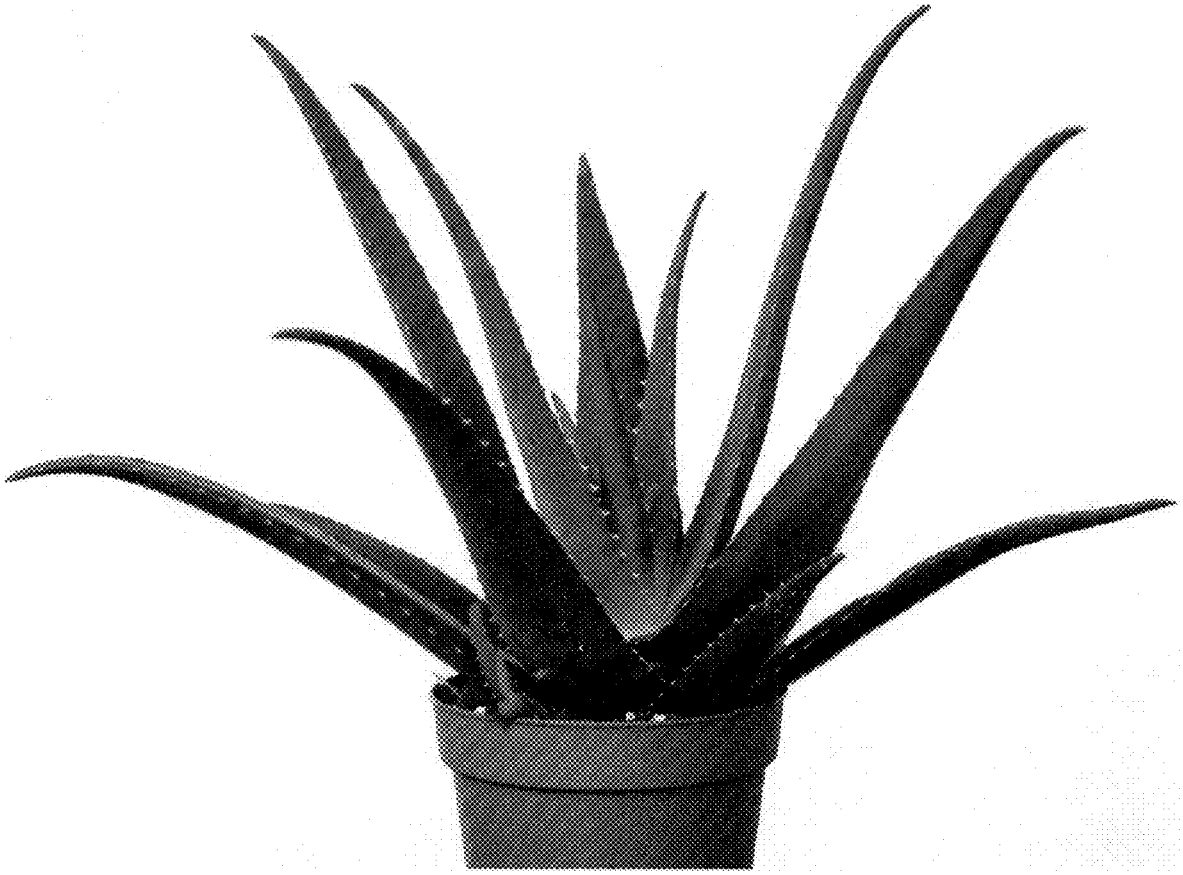
FIG. 1 illustrates, as nearly true as it is reasonably possible to make the same in color photographs of this type, an exemplary plant of 'AMIAL2136' grown in a commercial greenhouse in Honselersdijk, the Netherlands. This plant is approximately 40 weeks old, shown planted in a 14 cm container.
Figure 2:
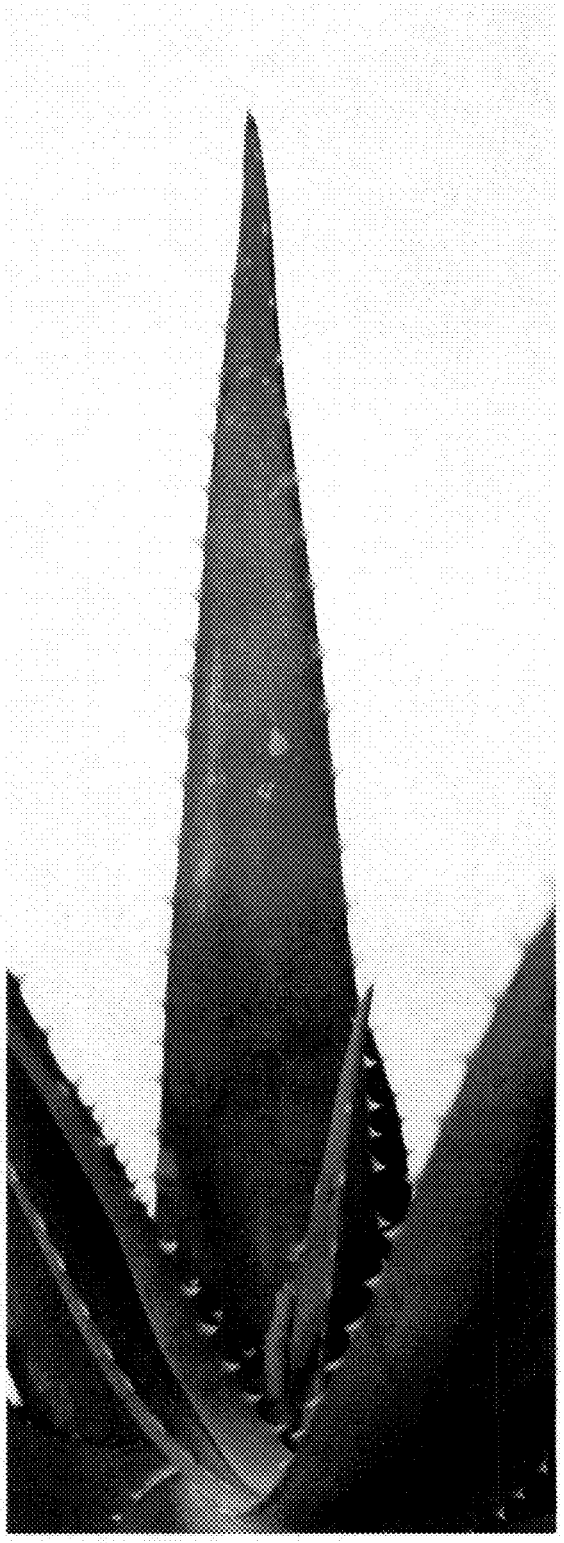
FIG. 2 illustrates, as nearly true as it is reasonably possible to make the same in color photographs of this type, adaxial surface of the mature foliage 'AMIAL2136'.
Figure 3:
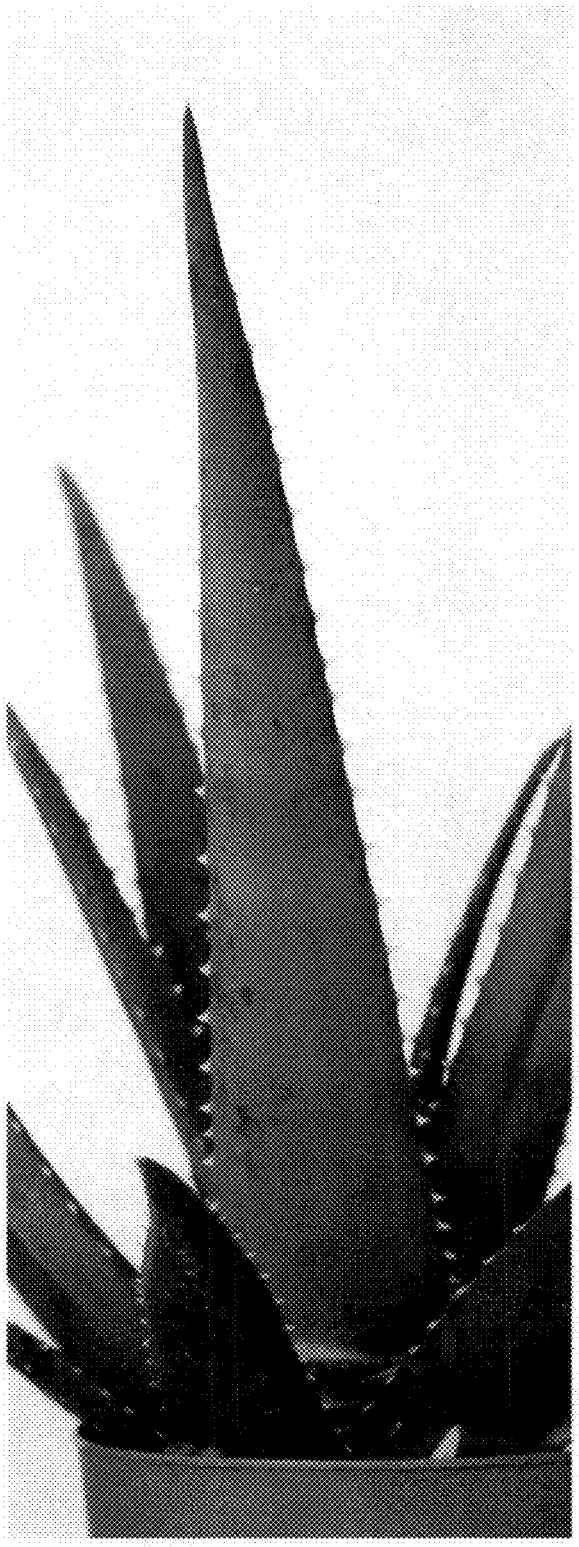
FIG. 3 illustrates, as nearly true as it is reasonably possible to make the same in color photographs of this type, the abaxial surface of the mature foliage of 'AMIAL2136'.

The following observations and measurements made in October of 2020 describe averages from a sample set of six specimens of 40-week-old 'AMIAL2136' plants grown in 14 cm nursery containers at commercial greenhouse in Honselersdijk, the Netherlands. Plants were produced using conventional greenhouse production protocols for *Aloe* which consisted of minimal overhead irrigation, minimal fertilizer applications, and pest and disease control measures for mealybugs and botrytis. No photoperiodic treatments or artificial light was given to the plants.

Those skilled in the art will appreciate that certain characteristics will vary with older or, conversely, with younger plants. 'AMIAL2136' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on The Royal Horticultural Society Colour Chart, The Royal Horticultural Society, London, Sixth Edition.

A botanical description of 'AMIAL2136' and a comparison with the parent plants and closest known comparator is provided below.

Plant description:

*Growth habit*.—Succulent perennial with foliage growing in a basal rosette; secondary rosettes are eventually produced at the base of the plant.

*Plant shape*.—Basal rosette.

*Height from soil level to top of foliar plane*.—25.0 cm.

*Plant spread*.—Average of 41.5 cm.

*Growth rate*.—Moderately to highly fast growing.

*Plant vigor*.—Highly vigorous.

*Propagation*.—Type — Leaf cuttings. Time to initiate rooting — Approximately 21 days at 18 degrees Celsius. Crop time — Approximately 60 weeks to produce a marketable plant in a 14 cm container.

*Disease and pest resistance or susceptibility*.—Plants have not been observed to be any more or less susceptible or resistant to pathogens and pests common to *Aloe* sp.

*Environmental tolerances*.—Adapt to, at least, USDA Zones 10 to 12 and temperatures as high as 40 degrees Celsius; low tolerance to rain; high tolerance to wind.

Root system:

*General*.—Thick; not fibrous.

*Texture*.—Slightly fleshy.

*Generic coloration*.—Greyed-red.

Stems: No stems observed at this date.

Foliage:

*Arrangement*.—Spiraled.

*Division*.—Simple.

*Attachment*.—Sessile.

*Quantity*.—Approximately 15 leaves per rosette.

*Shape*.—Lanceolate.

*Dimensions*.—28.3 cm long, 5.4 cm wide, and 1.1 cm thick, on average.

*Aspect*.—Flattened terete.

*Attitude*.—Upward with a slight bend outward at an approximate angle of 50 degrees, growing at a varying angle between 30 to 70 degrees distally from the base with leaf apices that are curved slightly downward at an average angle of 30 degrees to the leaf blade.

*Apex*.—Long and narrow acuminate.

*Base*.—Broad cuneate; decurrent.

*Margin*.—Dentate; no undulated or lobed. Spines have an average length of 0.3 mm and are colored greyed-green, nearest to RHS 192B, generally appearing as a near-white coloration.

*Texture, adaxial surface*.—Smooth, glabrous, non-rugose and glaucescent.

*Texture, abaxial surface*.—Smooth, glabrous, glaucescent; oldest leaves are sparsely to moderately covered with small, orbicular protuberances loosely arranged in irregular longitudinal rows; protuberance measurements are approximately 0.3 cm tall and 0.1 cm in diameter.

*Luster, adaxial surface*.—Matte.

*Luster, abaxial surface*.—Matte.

*Color*.—Juvenile foliage, adaxial surface — Green, nearest to RHS 137A; the epicuticular wax covering the leaf surface is green to greyed-green, nearest to in between RHS N138B and 191A. Juvenile foliage, abaxial surface — Green, nearest to RHS 137C; the epicuticular wax covering the leaf surface is green, nearest to in a blend of RHS N138A and N138B. Mature foliage, adaxial surface — Green to yellow-green, slightly darker than a blend nearest to RHS NN137A and 147A; the epicuticular wax covering the leaf surface is green to greyed-green, nearest to in between RHS N138B and 191A. Mature foliage, abaxial surface — Green, slightly darker than nearest to RHS NN137A; the epicuticular wax covering the leaf surface is green, nearest to in a blend of RHS N138A and N138B; protuberances and colored yellow-green, nearest to RHS 145B and 145C.

*Venation*.—No venation visible.

Inflorescence: No flowering has been observed to date.

Comparisons with the parent plant: Plants of the new cultivar 'AMIAL2136' differ from the seed parent, an unnamed *Aloe vera* plant (not patented) which typifies the species, in the following characteristics described in Table 1 below.

TABLE 1

| Characteristic | 'AMIAL2136' | The seed parent. |
|---|---|---|
| General coloration of the foliage. | A darker shade of green, relative to the seed parent. | A lighter shade of green, relative to 'AMIAL2136' |
| Size. | Larger than the seed parent. | Smaller than 'AMIAL2136'. |
| Foliage size. | Broader than the seed parent. | Narrower than 'AMIAL2136'. |
| Presence of foliar protuberances. | The abaxial surface of the oldest leaves are sparsely to moderately covered with small orbicular protuberances arranged in irregular longitudinal rows. | Both the adaxial and abaxial foliar surfaces of all foliage may be moderately to densely covered with round, oblong, or irregularly-shape protuberances. |

Plants of the new cultivar 'AMIAL2136' differ from the pollen parent, an unnamed *Aloe arborescens* plant (not patented) that typifies the species, in the following characteristics described in Table 2 below.

TABLE 2

| Characteristic | 'AMIAL2136' | The pollen parent. |
|---|---|---|
| Foliage attitude. | More upright than the pollen parent. | Less upright than 'AMIAL2136'. |
| Presence of foliar protuberances. | The abaxial surface of the oldest leaves are sparsely to moderately covered with small orbicular protuberances arranged in irregular longitudinal rows. | None present. |
| Foliage size. | Larger than the pollen parent. | Smaller than 'AMIAL2136'. |

TABLE 2-continued

| Characteristic | 'AMIAL2136' | The pollen parent. |
|---|---|---|
| General coloration of the foliage. | A lighter shade of green, relative to the pollen parent. | A darker shade of green, relative to 'AMIAL2136'. |

Comparisons with the closest known comparator: Plants of the new cultivar 'AMIAL2136' differ from the commercial plant, the species *Aloe humilis* (not patented), in the following characteristics described in Table 3 below.

TABLE 3

| Characteristic | 'AMIAL2136' | *Aloe humilis* |
|---|---|---|
| General coloration of the foliage. | Dark green. | Greyed-green. |
| Size. | Larger than the comparator. | Smaller than 'AMIAL2136'. |
| Foliage size. | Broader than the comparator. | Narrower than 'AMIAL2136'. |
| Presence of foliar protuberances. | The abaxial surface of the oldest leaves are sparsely to moderately covered with small orbicular protuberances arranged in irregular longitudinal rows. | Both the adaxial and abaxial foliar surfaces of all foliage is densely covered with relatively large, raised, spine-like protuberances. |

That which is claimed is:

1. A new and distinct variety of *Aloe* plant named 'AMIAL2136', substantially as described and illustrated herein.

* * * * *